United States Patent
Meaney et al.

(10) Patent No.: US 9,880,118 B2
(45) Date of Patent: Jan. 30, 2018

(54) PLANAR PROBE AND SYSTEM FOR MEASURING DIELECTRIC PROPERTIES OF BIOLOGICAL MATERIALS

(75) Inventors: Paul M. Meaney, Hanover, NH (US); Tina Zhou, Shenzhen (CN); Andrea Borsic, Lebanon, NH (US); Alexander T. Farkas, North Chatham, MA (US); Keith D. Paulsen, Hanover, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 1115 days.

(21) Appl. No.: 14/117,368

(22) PCT Filed: May 11, 2012

(86) PCT No.: PCT/US2012/037549
§ 371 (c)(1),
(2), (4) Date: Sep. 4, 2014

(87) PCT Pub. No.: WO2012/155057
PCT Pub. Date: Nov. 15, 2012

(65) Prior Publication Data
US 2014/0375337 A1    Dec. 25, 2014

Related U.S. Application Data

(60) Provisional application No. 61/485,591, filed on May 12, 2011.

(51) Int. Cl.
*G01R 31/00*    (2006.01)
*H01P 5/18*    (2006.01)
(Continued)

(52) U.S. Cl.
CPC .......... *G01N 27/02* (2013.01); *G01N 27/221* (2013.01); *G01N 33/4833* (2013.01); *G01N 33/49* (2013.01); *G01N 2333/435* (2013.01)

(58) Field of Classification Search
CPC .... G01N 27/02; G01N 33/49; G01N 33/4833; G01N 27/221; G01N 2333/435
(Continued)

(56) References Cited

U.S. PATENT DOCUMENTS 4,697,143 A * 9/1987 Lockwood ......... G01R 1/07342
                                                324/750.27
4,719,417 A    1/1988 Evans
(Continued)

FOREIGN PATENT DOCUMENTS

WO    2008145813 A1    12/2008
WO    2010099618 A1    9/2010

OTHER PUBLICATIONS

PCT Application PCT/US2012/037549 International Search Report and Written Opinion dated May 11, 2012, 9 pages.

*Primary Examiner* — Farhana Hoque
(74) *Attorney, Agent, or Firm* — Lathrop Gage LLP (57) ABSTRACT

A probe sensor has a printed circuit comprising a coplanar transmission line, a ground plane, a plated-through contact via, and a part-circular ring of ground vias surrounding the contact via. The coplanar transmission line and ground plane are formed on a first layer of the printed circuit, and the contact via and part-circular ring of ground vias are plated with a conductive biocompatible material on a second layer of the printed circuit. A system uses a network analyzer with the probe to measure electrical properties of biological tissue. Also described is a method of using the system to determine qualities of stored blood.

21 Claims, 9 Drawing Sheets

(51) Int. Cl.
*G01N 27/02* (2006.01)
*G01N 27/22* (2006.01)
*G01N 33/483* (2006.01)
*G01N 33/49* (2006.01)

(58) Field of Classification Search
USPC .............................. 324/756.03, 649; 333/116
See application file for complete search history.

(56) References Cited

U.S. PATENT DOCUMENTS

| | | | | |
|---|---|---|---|---|
| 5,629,654 | A | * | 5/1997 | Frick ........................ H01P 5/186 |
| | | | | 333/116 |
| 2001/0019271 | A1 | * | 9/2001 | Scott ....................... G01N 22/00 |
| | | | | 324/637 |
| 2004/0040868 | A1 | | 3/2004 | Denuzzio et al. |
| 2010/0058846 | A1 | * | 3/2010 | Tanbakuchi ........... B82Y 35/00 |
| | | | | 73/105 |
| 2011/0175627 | A1 | * | 7/2011 | Kleismit ................ B82Y 20/00 |
| | | | | 324/637 |

* cited by examiner

PLANAR PROBE AND SYSTEM FOR MEASURING DIELECTRIC PROPERTIES OF BIOLOGICAL MATERIALS

RELATED APPLICATIONS

The present application claims priority to U.S. Provisional Patent Application No. 61/485591 filed 12 May 2011, which is incorporated herein by reference.

GOVERNMENT INTEREST

This invention was made with government support under Grant #POI-CA080139 awarded by the National Institutes of Health/National Cancer Institute. The government has certain rights in the invention.

FIELD

The present document relates to the field of devices for measurement of dielectric properties of biomaterials, including human and animal tissue and blood.

BACKGROUND

It is known that biological materials, including human and animal tissue and blood, have dielectric properties that vary somewhat with the type of tissue. These dielectric properties include permittivity, and conductivity.

Tissue-specific dielectric properties have historically often been measured with a probe formed from a straight section of coaxial transmission line having an open, unterminated, end that is applied to the tissue. A coaxial probe of this type having diameter of 0.085 inch is, for example, described for use between 10 MHz and 10 GHz in T. Whit Athey, et al. IEEE Transactions on Microwave Theory and Techniques, Vol. MTT-28, NO. 4, APRIL 1980, Measurement of Radio Frequency Permittivity of Biological Tissues with an Open-Ended Coaxial Line: Part I. Using such probes, dielectric properties of tissues were found to differ between kidney, muscle, brain, fat, and other tissue types.

Using coaxial probes of various designs, dielectric properties of tissue in the range 10 kHz to 1 MHz have been shown to differ between cancerous and non-cancerous tissues within a human breast, as reported in Ryan J Halter, et al. Physiol. Meas. 30 (2009) S121-S136 The correlation of in vivo and ex vivo tissue dielectric properties to validate electromagnetic breast imaging: initial clinical experience (Halter). The intraoperative coaxial probe used in-vivo by Halter was limited to the 10 to 100 kHz range, however measurements on removed breast tissue indicated that differences in dielectric properties of at least some tumor types and breast stroma also exist at higher frequencies into at least the low MHz range.

There are potential advantages of measuring electrical parameters of tissue in the microwave frequency range, in particular between 100 MHz and 10 GHz. At lower frequencies, differences between permittivity and conductivity may be related to intracellular and extracellular water. At these higher frequencies above 100 MHz, it is possible to quantify total tissue water and to discriminate between free and chemically-bound water in the tissue.

SUMMARY

A probe sensor has a printed circuit board having a coplanar transmission line and a first ground plane on a first layer of the board. A center conductor of the transmission line couples to a plated-through contact via, and a part-circular ring of ground vias surrounds the contact via. The contact via passes through the board to a second surface of the board. A round, circular, insulating gap surrounds the plated-through contact via on the second surface of the board, and is surrounded by a metal contact ring that connects to the first ground plane through the part-circular ring of ground vias. In some embodiments the metal contact ring is plated with a conductive biocompatible material. Remaining area of the second layer is a second ground plane electrically coupled to the metal contact ring.

A blood collection and transfusion set has a blood collection reservoir bag having a probe attached thereto. The probe has a printed circuit comprising a coplanar transmission line, a ground plane, a plated-through contact via, and a part-circular ring of ground vias surrounding the contact via. The coplanar transmission line and ground plane are formed on a first layer of the printed circuit, and the contact via and part-circular ring of ground vias are plated with a noncorrosive, conductive, biocompatible material on a second layer of the printed circuit. The probe is adapted for coupling through a cable to a network analyzer for measuring dielectric properties of any blood within the collection reservoir bag.

A method of verifying blood quality includes collecting blood in a collection and transfusion set comprising a blood collection reservoir bag having a probe attached thereto. The probe is fabricated on a printed circuit card with a coplanar transmission line, a ground plane, a plated-through contact via, and a part-circular ring of ground vias surrounding the contact via. The coplanar transmission line and ground plane are formed on a first layer of the printed circuit, and the contact via and ground contact ring, and part-circular ring of ground vias are in some embodiments plated with a noncorrosive, conductive, biocompatible material on a second layer of the printed circuit, this noncorrosive plating does not short circuit the contact via to the ground contact ring. The contact via and part-circular ring contact blood in the reservoir bag. Provided is apparatus for reading a unique identifier from a machine-readable label of the collection and transfusion set. A network analyzer is attached to the probe and an initial set of electrical parameters of the blood is obtained and stored with the unique identifier in a memory. At a later date, the network analyzer is reconnected to the probe and the unique identifier is read from the machine-readable label of the collection and transfusion set, and the unique identifier is used to locate the initial set of electrical parameters. A second set of electrical parameters is obtained from the blood and compared to the initial set of parameters; and the difference is compared to limits—if the difference exceeds limits the blood may be discarded instead of transfused into a patient.

DETAILED DESCRIPTION OF THE EMBODIMENTS

Figure 1:
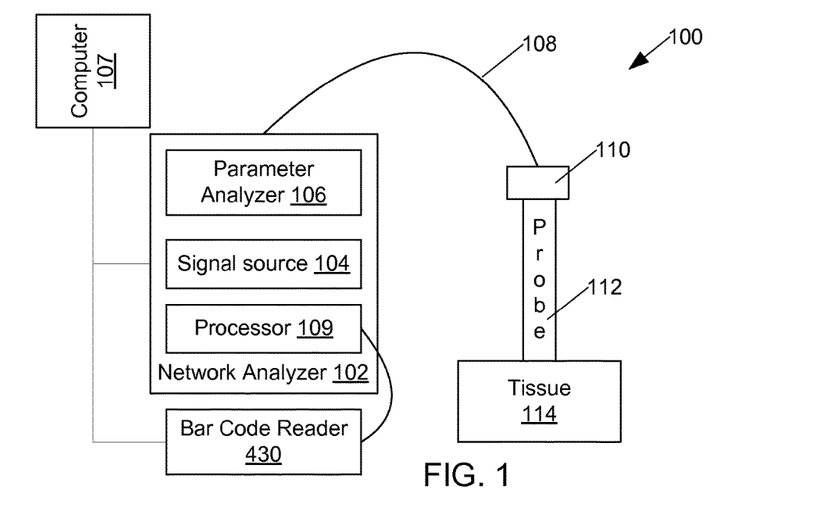
FIG. 1 is a block diagram of a system for measuring dielectric properties of tissue.

A system 100 for measuring dielectric properties of tissue is illustrated in FIG. 1. The system typically includes a network analyzer 102 having a signal source 104 and a parameter analyzer 106 as well as a processor 109. Network analyzer 102 couples through a coaxial cable 108 and a connecting device or devices 110 to a probe 112. Probe 112 in turn couples to the tissue to be measured 114. The signal source 104 provides a microwave signal through cable 108 to probe 112 and into tissue 114, and parameter analyzer 106 observes reflections, including phase shift, and magnitude of the reflections relative to stimulus, to determine permittivity and conductivity properties of tissue 114. In an embodiment, network analyzer 109 operates under control of, and provides measured parameter information including S-parameters to, a handheld, notebook, or desktop computer 107, which uses calibration information to translate measured parameter information into measured tissue parameters.

Figure 2:
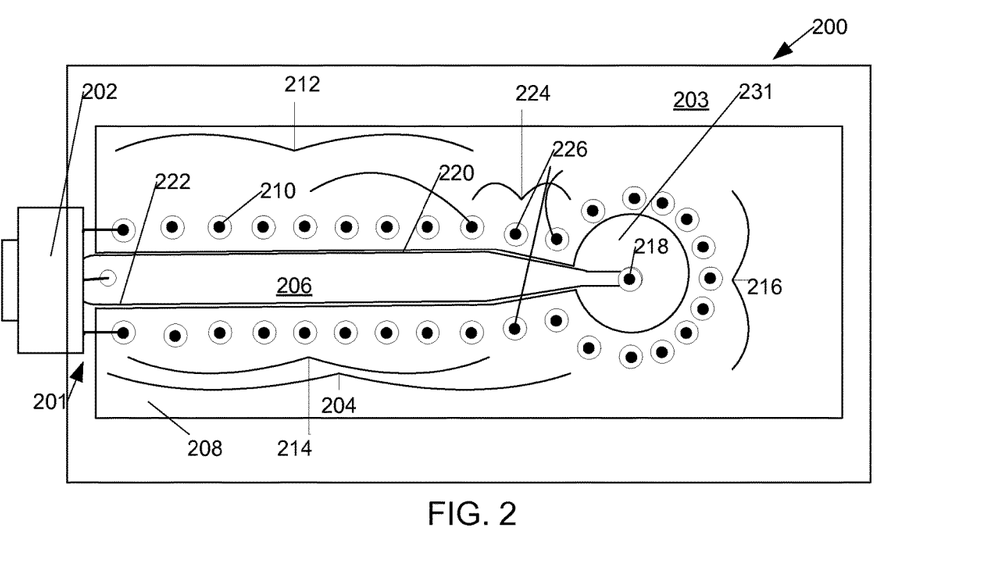
FIG. 2 is a plan view of a printed circuit probe for measuring dielectric properties of tissue.
Figure 3:
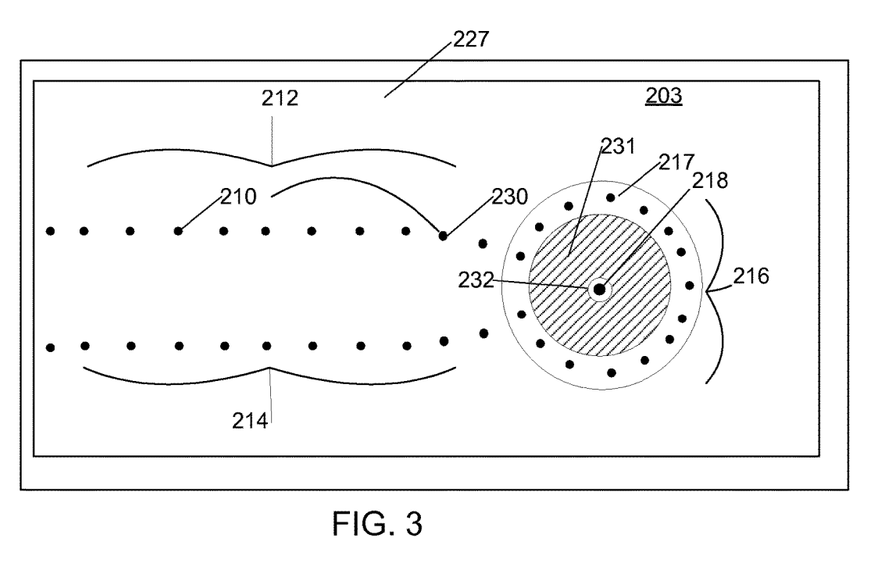
FIG. 3 illustrates a second side of the printed circuit probe of FIG. 2.

A new probe 200 is illustrated in FIGS. 2 and 3; probe 200 is for use in place of probe 112 in a system resembling that of FIG. 1. In an embodiment, the probe is fabricated from a two-layer FR4 printed circuit board material, having a substrate 203. A first or bottom layer of the two layers, as illustrated in FIG. 2, has an area 201 for attaching connecting device 202 that is in turn adapted for coupling with a connector on a coaxial cable, which in turn may connect to network analyzer 102. Connecting device 202 couples to a first end of coplanar waveguide portion 204 having a center conductor 206 and a ground plane 208 both fabricated from conductive foil on a first layer of the printed circuit as illustrated in FIG. 2. In alternative embodiments, the probe is fabricated from other types of printed circuit material, including in some embodiments flexible printed materials.

Ground plane 208 has a first row 212 of multiple plated-through via holes 210 near a first side of center conductor 206, and a second row 214 of plated-through via holes near a second side of center conductor 206. Each plated-through via hole may be a center of a small ring of metal foil on a second layer of the board material, or alternatively a ground plane may be provided on the second layer of the board material, as illustrated in FIG. 3. Further plated-through ring via holes from ground plane 208 form a partial circle 216 around a tissue-connector via hole 218, tissue-connector via hole 218 is electrically connected to a second end of center conductor 206. Partial circle 216 of via holes from ground plane 208 couple to a ground ring tissue contact 217 on the second layer of the board material. For purposes of this document, a part-circular ring of vias means multiple vias laid out in a pattern that describes more than half of, and typically three quarters or most of, a circle, or a shape approximating a circle, the circle approximately centered on the contact via. The part-circular ring may have a gap in the pattern, such as a gap that permits the coplanar transmission line to reach the plated-through contact via without interference from a via of the pattern.

Center conductor 206 is electrically isolated from ground plane 208 by gaps 220, 222 throughout the coplanar waveguide portion 204. Gap width, spacing from ground plane 208 to center conductor 206, is determined to produce a characteristic impedance of the coplanar waveguide portion 214 of fifty ohms. In a particular embodiment, the center conductor has 85 mils width in portions between the coupling device 202 and the tapering portion 224, with a gap of width 8 mils and fabricated on a substrate PCB material 60 mils thick. Vias 210 are formed on plated-through holes drilled with 19.7 mils diameter. Vias such as the contact via 218 not within larger metal shapes are centered within round pads of 35.7 mils diameter, such as foil pad 232, on each layer. These round pads may, however, be merged into other shapes such as ground plane 208, ground ring tissue contact 217, or center conductor 206 and, if those shapes are sufficiently large, effectively vanish into those shapes.

The coplanar waveguide is sized by using thickness t in the equations for a thickness correction factor:

$$\Delta = \frac{1.25t}{2\pi} \cdot \left(1 + \ln\left(\frac{4\pi W}{t}\right)\right)$$

$$W_e = W + \Delta$$

$$S_e = S - \Delta$$

$$k_e = k_1 + (1 - k_1^2) \times \frac{\Delta}{2S}$$

$$k_1 = \frac{W}{(W + 2S)}$$

Where K is an elliptical integral of first kind, K' a first derivative of the elliptical integral of the first kind. These are elliptical integrals. Also, where W is an actual width of the center conductor of the transmission line, $W_e$ is an effective width of the center conductor of the transmission line, S is spacing between the center conductor and the ground conductor on each side of the center conductor and $S_e$ is the effective spacing. Further $k_e$ is an effective modulus.

Where t is a thickness of metal foil on the board, and $\Delta$ a correction factor for foil thickness, and these correction factors are used to calculate an impedance Z of approximately fifty ohms using the impedance equation:

$$Z = \frac{60\pi}{\sqrt{\varepsilon_{re}}} \cdot \frac{1}{\frac{K(k_1)}{K'(k_1)} + \frac{K(k_3)}{K'(k_3)}}$$

where $k_3$ is defined as:

$$k_3 = \frac{\tanh\left(\frac{\pi W}{4h}\right)}{\tanh\left(\frac{\pi(W+2S)}{4h}\right)}$$

and h is the thickness of the substrate, and $$\in_{re} = 1 + q \cdot (\in_r - 1)$$

where $\in_{re}$ is the relative permittivity and q is the filling factor:

$$q = \frac{\frac{K(k_3)}{K'(k_3)}}{\frac{K(k_1)}{K'(k_1)} + \frac{K(k_3)}{K'(k_3)}}$$

The coplanar waveguide effectively terminates in a short coaxial line formed by plated through via 218, ground ring tissue contact 217, and with the vias of semicircular row 216 of vias acting as a shield. This short line also has a characteristic impedance of about 50 ohms, as determined by solving the equation below for semicircular row diameter and via diameter:

$$Z_0 = \frac{138}{\sqrt{\varepsilon_R}} \log\left(\frac{D}{d}\right) \text{ohms}$$

Where $\in_R$ is effective permittivity of the board material, D is inner diameter of the ground ring tissue contact 217 and represents the outer diameter of the dielectric surrounding the center conductor of an effective coaxial transmission line formed by the contact via and the ground ring tissue contact 217, and directed through the PC board as the semicircular row 216 of vias. The semicircular row of vias 216 and ground ring contact 217 form an effective, albeit interrupted, outer conductor of the effective coaxial line, and "d" is a diameter of the contact via 218 forming a center conductor of the effective coaxial transmission line. Dielectric of the effective coaxial transmission line is represented by a gap 231 between the metal foil 232 surrounding the contact via 218 and metal of the ground ring contact 217.

Coplanar waveguide 204 includes a tapering portion 224 where center conductor 206 tapers from an initial width to a width resembling that of contact via 218. Tapering portion 224 adapts center conductor width 206 from a first width suitable for coupling to connecting device 202 to a second width suitable for coupling to tissue-connector plated-through via hole 218, and the second width is approximately equal to a diameter of plated-through via hole 218 as surrounded by a minimum-width ring of foil. Tapering portion 224 is surrounded by gaps 220, 222, which narrow in tapering portion 224 to maintain equivalent characteristic impedance of fifty ohms to match impedance of remaining portions of coplanar waveguide 214. Tapering portion 224 is surrounded by additional via holes 226 in ground plane 208 and which are spaced at approximately the same distance from gaps 220, 222 as via holes of the first 212 and second 214 rows. Via holes 226 make contact with a ground plane 227 on a second layer of the PCB. It is desirable that the ground planes 227 and 208 be intimately connected through these via holes.

In a particular embodiment, center conductor 206, ground plane 208, and first layer side of via holes 210 are all covered with a nonconductive passivating material except for a portion near the first end for attaching connecting device 202. Similarly, via holes 210 and surrounding foil in some embodiments are covered with a nonconductive, biocompatible, insulating, passivating material over the second layer except for tissue connector via hole 218, its surrounding foil ring 232, and ground contact ring 217 including via holes of partial circle 216. Foil of ground contact ring 217 is not covered with insulating passivating material. In some embodiments, tissue connector via hole 218, surrounding foil ring 232, and ground contact ring 217 are plated with a biocompatible, corrosion-resistant, metal such as gold or chrome to permit long term contact to tissue without adverse tissue reaction or contact resistivity changes. In alternative embodiments, such as those intended for short term use, via hole 218, foil ring 232, and ground contact ring 217 are left as bare copper foil.

A dielectric ring 231, bare of metal on both sides except for center conductor 206 and tissue connector via hole 218 and a foil ring 232 surrounding tissue connector via hole 218, surrounds the tissue connector via and lies within ground contact ring 217.

In an embodiment, substrate 203 is a rigid glass-fiber printed circuit substrate material such as but not limited to that material known in the industry as FR4. In an alternative embodiment, substrate 203 is a flexible printed-circuit substrate material such that probe 200 is flexible.

Figure 2A:
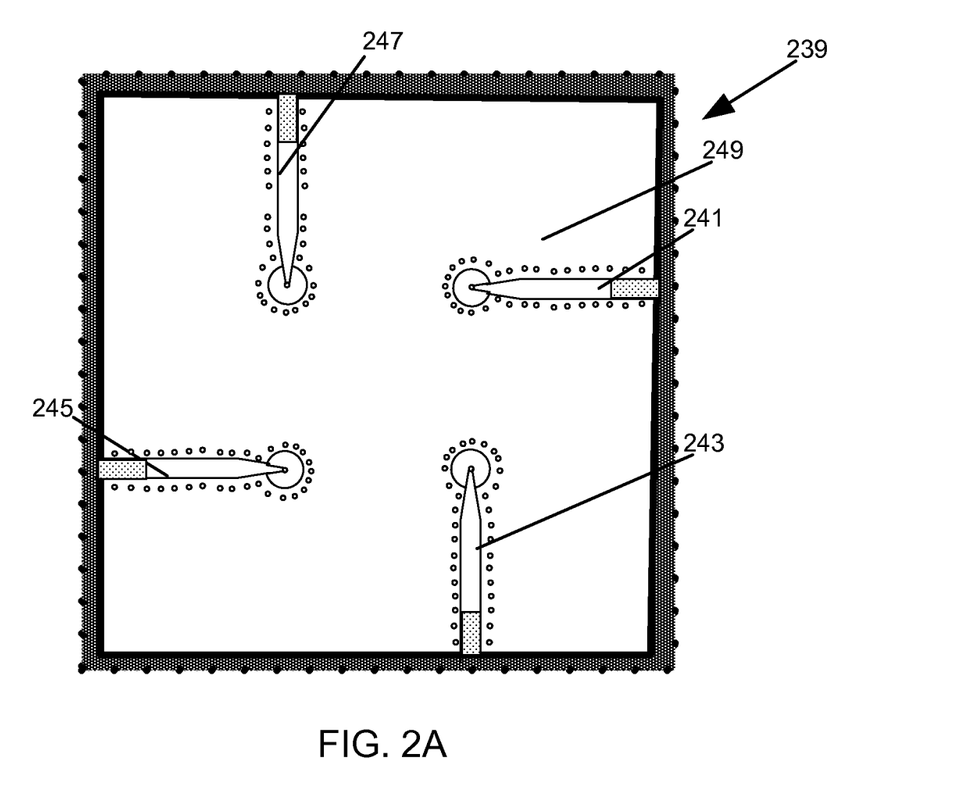
FIG. 2A is a photograph of a printed circuit having four probes for measuring dielectric properties of tissue.

Multiple copies of the probe of FIG. 2 and FIG. 3 may be fabricated on a single printed circuit card 239. The photograph of FIG. 2A illustrates four probes 241, 243, 245, 247 on a single card, positioned to bring contacts from a four-channel network analyzer to a small sample of tissue positioned to cover box 249.

Figure 4:
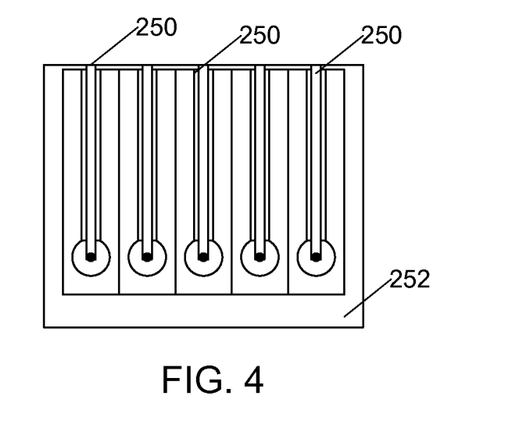
FIG. 4 illustrates a multiple-contact probe for measurement of dielectric properties of tissue at surgical margins to determine if and where tumor remains.

As illustrated in FIG. 4, probes of the design of FIGS. 2 and 3 may be formed as a linear strip of probes 250 on a single substrate 252, in an embodiment ground plane 208 is common to all probes of a strip, in an alternative embodiment ground plane 208 for each probe is electrically isolated from ground plane 208 of adjacent probes.

Figure 4A:
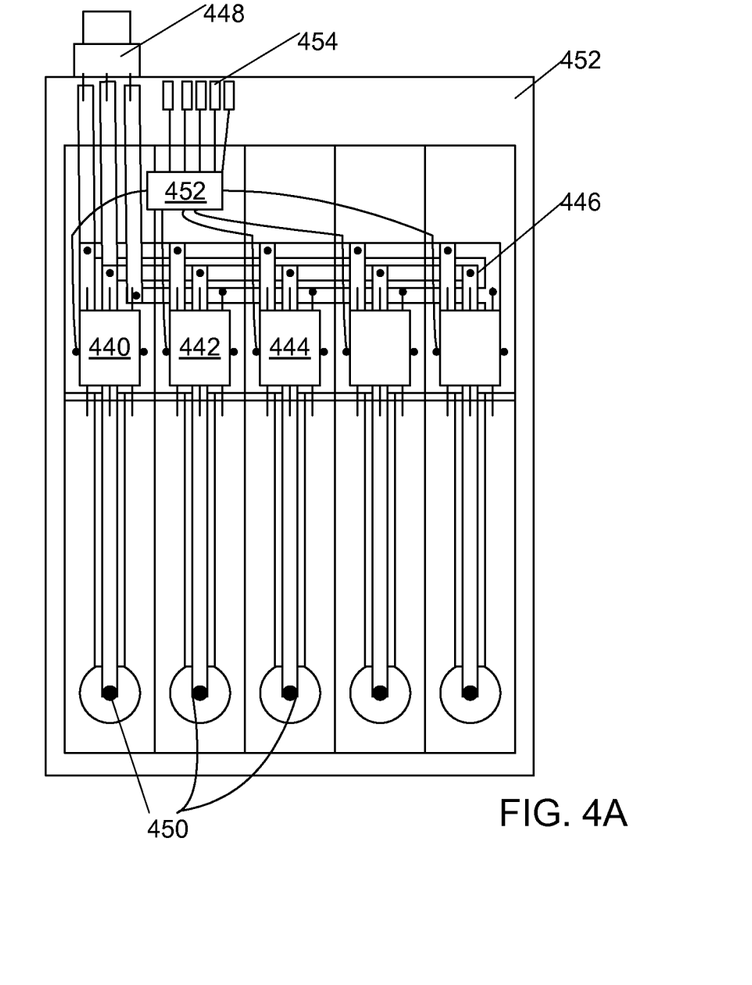
FIG. 4A illustrates a multiple-contact probe for measurement of dielectric properties of tissue integrated with electronic switches

In an alternative embodiment illustrated in FIG. 4A, probes 450 of the design of FIGS. 2 and 3 are formed on a single PC board 452 as a linear array. Attached to each probe 450 is a single-pole P-Intrinsic-N (PIN) diode microwave-frequency switch 440, 442, 444 as illustrated in FIG. 4A. Each switch 440, 442, 444 is coupled to, when turned on, pass signals between one of probe 450 and a coplanar transmission-line RF bus 446 in turn coupled to single SMA connector 448. Switches 440, 442, 444 are controlled by an on-board decoder 452, operated through a logic connector 454 such that only one probe 450 is electrically coupled to the SMA connector at any one time.

In operation, the device of FIG. 4A is coupled to a network analyzer through a coaxial cable connected to the SMA connector 448. Each probe is calibrated by using the network analyzer to measure parameters in probes-open, probes shorted, and probes-in-water conditions separately to quantify reflections, losses, and other electrical parameters of the on-board 454 interconnect, such as RF bus 446, and switches 440, 442, 444. The measurements of parameters under all three (open, shorted, and probes-in-water) conditions are used by computer 107 to determine characteristics of the probe so that these characteristics can be subtracted from characteristics determined from measured parameters of tissue. Once calibrated, the device may be placed against tissue and dielectric properties of the tissue measured by enabling each switch 440, 442, 444 in sequence. In an alternative embodiment, an additional calibration point is obtained by pressing the probes against a calibration phantom having a gel having known permittivity and conductivity.

Figure 5:
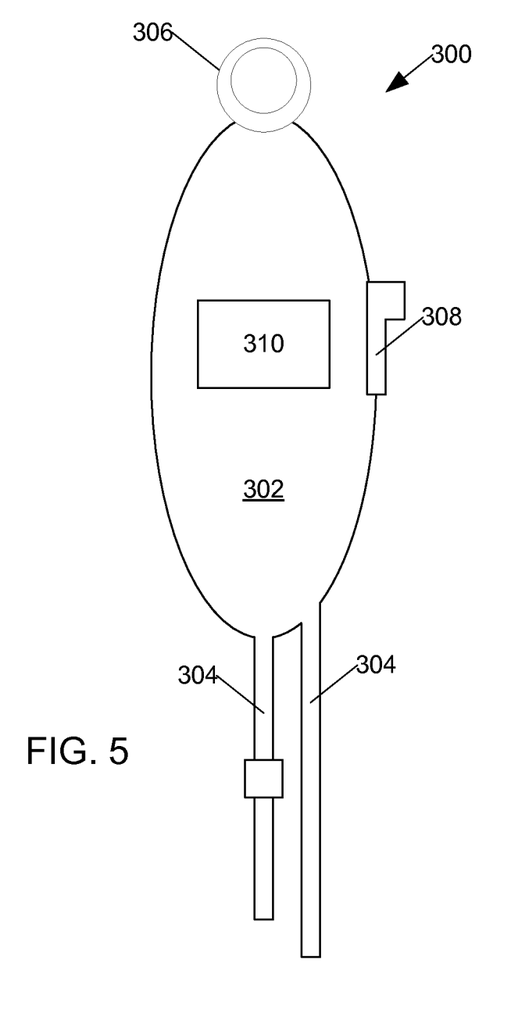
FIG. 5 illustrates a blood transfusion set with an integral probe for measurement of dielectric properties of blood.

In an embodiment, a blood collection and transfusion set 300, as illustrated in FIG. 5, has a disposable reservoir 302, one or more tubing 304 sections adapted to permit filling of set 300, to provide samples for typing and crossmatch, and to permit infusing of contents into a subject, and a suspension loop 306 for attachment to a stand as known in the art of blood transfusion sets. The set 300 also has a probe 308 as heretofore described with reference to FIG. 2 and FIG. 3 and fabricated on a flexible integrated circuit material molded into a side of reservoir 302 such that the biocompatible plating on tissue connector via hole 218 is in contact with reservoir 302 contents. Reservoir 302 also has a human-readable and bar-coded label 310.

Figure 6:
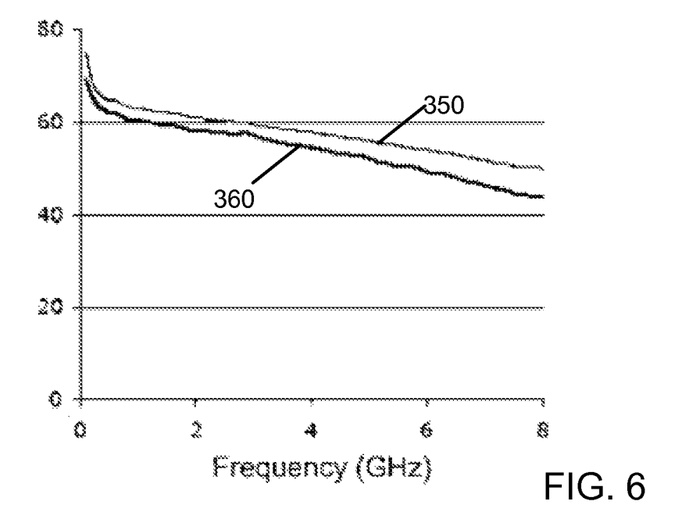
FIG. 6 illustrates changes in permittivity of blood with age of the blood for a particular sample of human blood.
Figure 7:
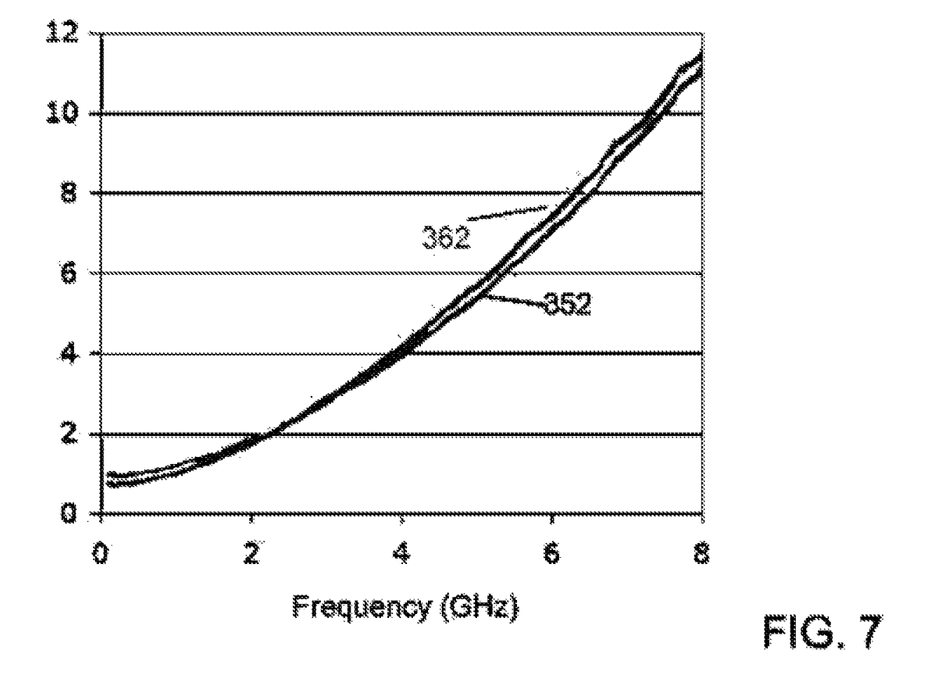
FIG. 7 illustrates changes in conductivity of blood with age of the blood for the same sample of blood as used in FIG. 6.

It has been found that the permittivity of blood, as illustrated in FIG. 6, changes with age. For example, fresh blood has permittivity 350 over a range of 0.1 to 8 GHz that differs significantly from permittivity 360 of 9 week old blood. It has been observed that conductivity (FIG. 7) also changes with age, fresh blood 352 having different conductivity than aged blood 362, and thus are believed to be indicative of a degradation process in blood in reservoir 302. While permittivity has been observed to change with age for at least one blood sample, quantifying the extent of changes and correlating these changes to degradation of the blood to determine rejection thresholds will require additional work.

Figure 8:
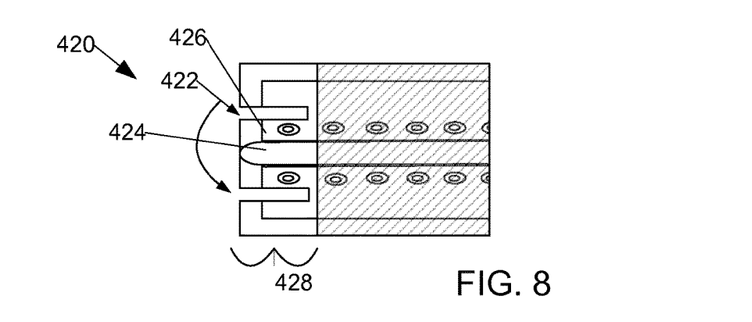
FIG. 8 illustrates a printed circuit probe having notches for alignment to a spring-clip connecting device.

A probe 420 illustrated in FIG. 8 resembles that of FIG. 2 and FIG. 3 but is fabricated on a flexible printed circuit material with a pair of guide notches 422 straddling the center conductor 424 and a central portion of the ground plane 426. The embodiment of FIG. 8 has a plating of gold, or another conductive, corrosion resistant, material, in a region 428 near the first end of both the ground plane and center conductor, this region 428 forming a connecting device. The remainder of the probe is as previously described with reference to FIG. 2 and FIG. 3.

Figure 9:
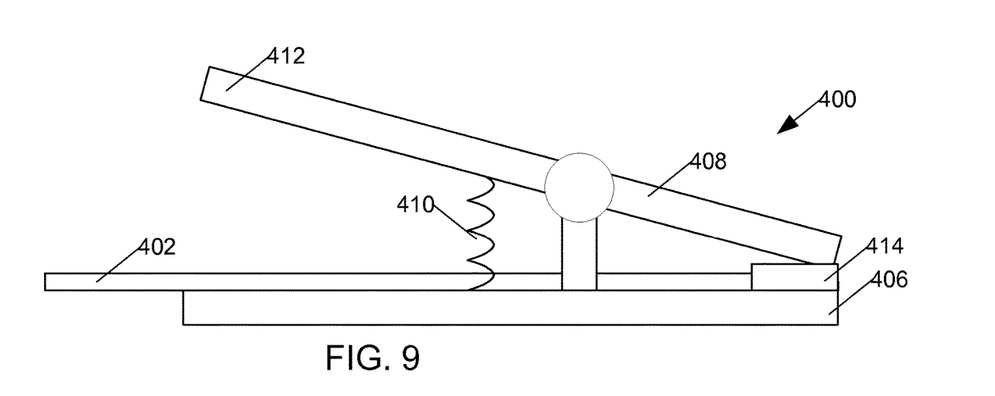
FIG. 9 is a side view of a spring-clip connecting device for coupling a cable from a network analyzer to a printed circuit probe of FIG. 2.
Figure 10:
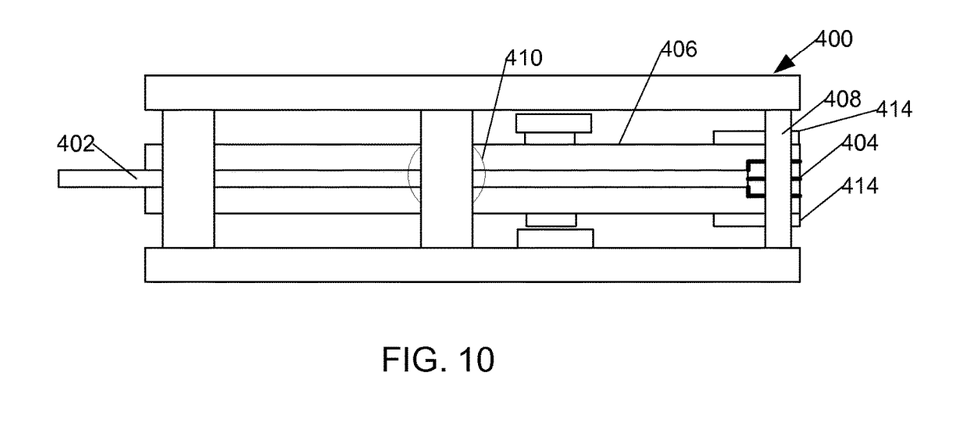
FIG. 10 is a top view of the spring-clip connecting device of FIG. 8.

The probe of FIG. 8 is intended for use with the spring-clip connecting device 400 of FIG. 9 and FIG. 10, the spring clip connecting device coupled through cable 402 to a portable network analyzer 102 (FIG. 1). In a particular embodiment, the portable network analyzer also has a barcode reader 430 for reading label 310 of the blood collection and infusion set 300 (FIG. 5), and the probe 420 is mounted on reservoir 302 as probe 308, and bar-code reader 430 is also in communication with computer 107.

Clip 400 has electrodes 404 plated with corrosion resistant metal such as gold and adapted for coupling to the plated regions of center conductor 424 and ground plane 426 of probe 420. These electrodes 404 are connected to cable 402. Clip 400 also has a handle portion 406 hinged to a clamp portion 408, and a spring 410 that acts to press a grip region of clamp portion 408 against electrodes 404 and handle portion 406. Handle portion 406 has guides 414 for engagement with guide notches 422 of probe 420. A grip portion 412 of clamp portion 408 is manually pressed to open a gap between the grip region of clamp portion 408 and electrodes 404, the probe 420 is inserted into this gap such that notches 422 engage with guides 414 and electrodes 404 engage with the plated surfaces of center conductor 424 and ground plane 426. The grip portion 412 is then released to allow grip region of the clamp portion 408 to press on probe 420 retaining probe 420. Tissue electrical parameters may then be read by the network analyzer through cable 402 and probe 420.

In an alternative embodiment, each of notches 422 and guides 414 differ in size, such that probe 420 will fit into clip 400 in only one way, thereby permitting contacts 404 to make contact with the plated surfaces of center conductor 424 and ground plane 426 but preventing contacts 404 from being pressed against an opposite side of printed circuit probe 420 that lacks these structures.

In an alternative embodiment, a cam and lever replaces spring 410 and grip portion 412 of clamp portion 408.

In an alternative embodiment, clip 400 is adapted to simultaneously engage contacts coupled from several cables to several probes simultaneously. Such an embodiment is particularly well suited for use with the embodiment of FIG. 4 or similar probe-array embodiments.

A method of ensuring transfusion blood quality involves collecting blood in the collection and transfusion set 300. Once collected, spring clip 400 of the portable network analyzer is attached through clip 400 to probe 308, and the label 310 of set 300 is read with bar code reader 430. Label 310 has a machine readable identification, in alternative embodiments label 310 has a unique bar code identification, and in other embodiments a radio frequency identification circuit capable of transmitting a unique machine readable identification. An initial set of electrical parameters of the blood is thereupon read and stored in a memory of a computer 107 attached to the network analyzer, together with an identification read from the label 310. When a transfusion is desired, type and crossmatch is performed in the manner known in the art. The portable network analyzer is attached through clip 400 to probe 308, and a second set of electrical parameters of the blood is determined. Label 310 of set 300 is read with bar code reader 430 and the initial set of electrical parameters of the blood is read from the memory and compared with the second set of parameters; if the initial and second set of parameters differ by more than a predetermined threshold amount a "spoiled blood" indication is provided on a display of the computer, whereupon the blood is rejected as having deteriorated or spoiled, and other blood is used for any desired transfusion.

In an embodiment, the network analyzer provides a microwave signal at a preselected frequency between 100 MHz and 10 GHz and measures both amplitude and phase of reflections from the probe. The amplitude and phase of reflections are then used by the analyzer or attached computer 107 to calculate permittivity and conductivity of any tissue that may be in contact with the probe. The computer then uses the analyzer to repeat the measurements and calculations for additional frequencies within the desired frequency range.

A method of ensuring adequate surgical margins during surgery, thereby ensuring adequate removal of a malignant tumor from a subject, is for a surgeon to remove a block of tissue from the subject that is thought to have adequate surgical margins. An embodiment having multiple probes such as that of FIG. 4 or FIG. 4A is then pressed against edges of the block of tissue, and each probe is coupled in sequence to a network analyzer to measure dielectric properties of tissue at each probe and to convey those measurements to computer 107. Probes providing tissue dielectric properties resembling tumor are then identified to the surgeon, these probes are indicative of locations on the block of tissue that may have inadequate surgical margins. Should it be practical to do so, the surgeon may then remove additional tissue from the subject corresponding to those identified locations of suspected inadequate surgical margins.

In an alternative method of ensuring adequate surgical margins during surgery, thereby ensuring removal of a malignant tumor, is for a surgeon to press an embodiment having a strip of multiple probes of FIG. 4 or of FIG. 4A against suspect edges of the incision, to couple each probe to a network analyzer in sequence, to measure dielectric properties of tissue at each probe, to compare the dielectric properties against other measurements of dielectric properties of tissue and tumor and limits, and for the computer to present an alarm when those dielectric properties differ from expected properties of normal stroma or of measured properties obtained from adjacent probes by more than a predetermined limit.

When probing surfaces of a surgical cavity, or of a removed surgical specimen, to determine adequacy of surgical margins, it is convenient to use a rectangular array of probes to allow probing many locations on a surface with one manual probe placement, this is expected to be faster than using either a single probe or the strip of probes of FIG. 4. A printed circuit board 500 (FIG. 11, top view showing coplanar transmission lines of a top layer) has an incoming coplanar transmission line 502 for coupling to the network analyzer. The printed circuit board also has at least one analog multiplexor integrated circuit 504, 506, and in the illustrated embodiment multiple analog multiplexor circuits; in the illustrated embodiment a first stage of analog multiplexor 506 couples the incoming transmission line 502 through intermediate coplanar transmission lines 508 to a selected one of a second stage analog multiplexors 504. Each second stage multiplexor 504 couples its incoming intermediate coplanar transmission line 508 to a selected coplanar transmission line 510 leading to a probe. In an embodiment each analog multiplexor 504, 506 is a 4:1 analog multiplexor, although in alternative embodiments 8:1, 16:1, or other configurations of analog multiplexors may be used in either a single stage or in multiple stages. In order to ensure function, additional wiring, such as power and chip-select wiring (not shown) for operating the analog multiplexors, may be present on the top layer.

Figure 11:
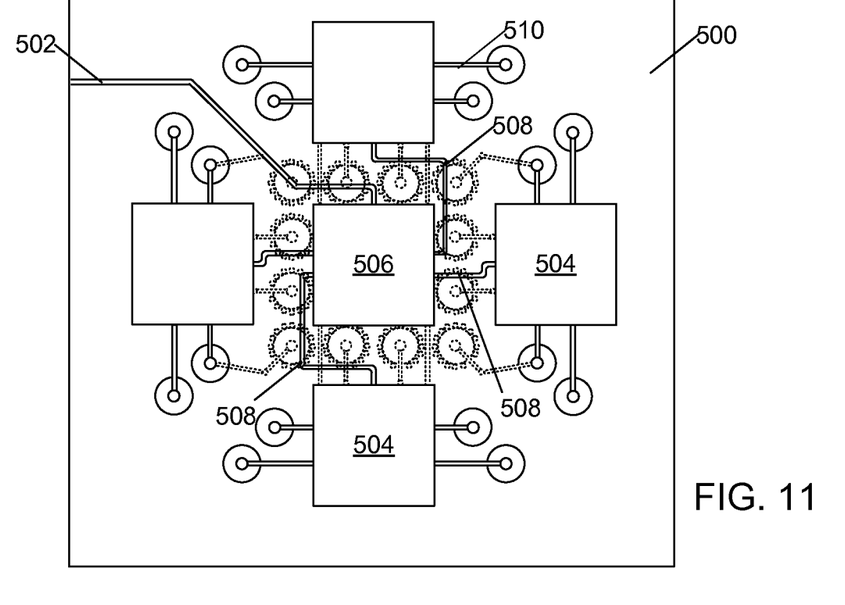
FIG. 11 is a top view of a multilayer printed circuit having analog switches on a top surface and an array of probes on a bottom surface.
Figure 12:
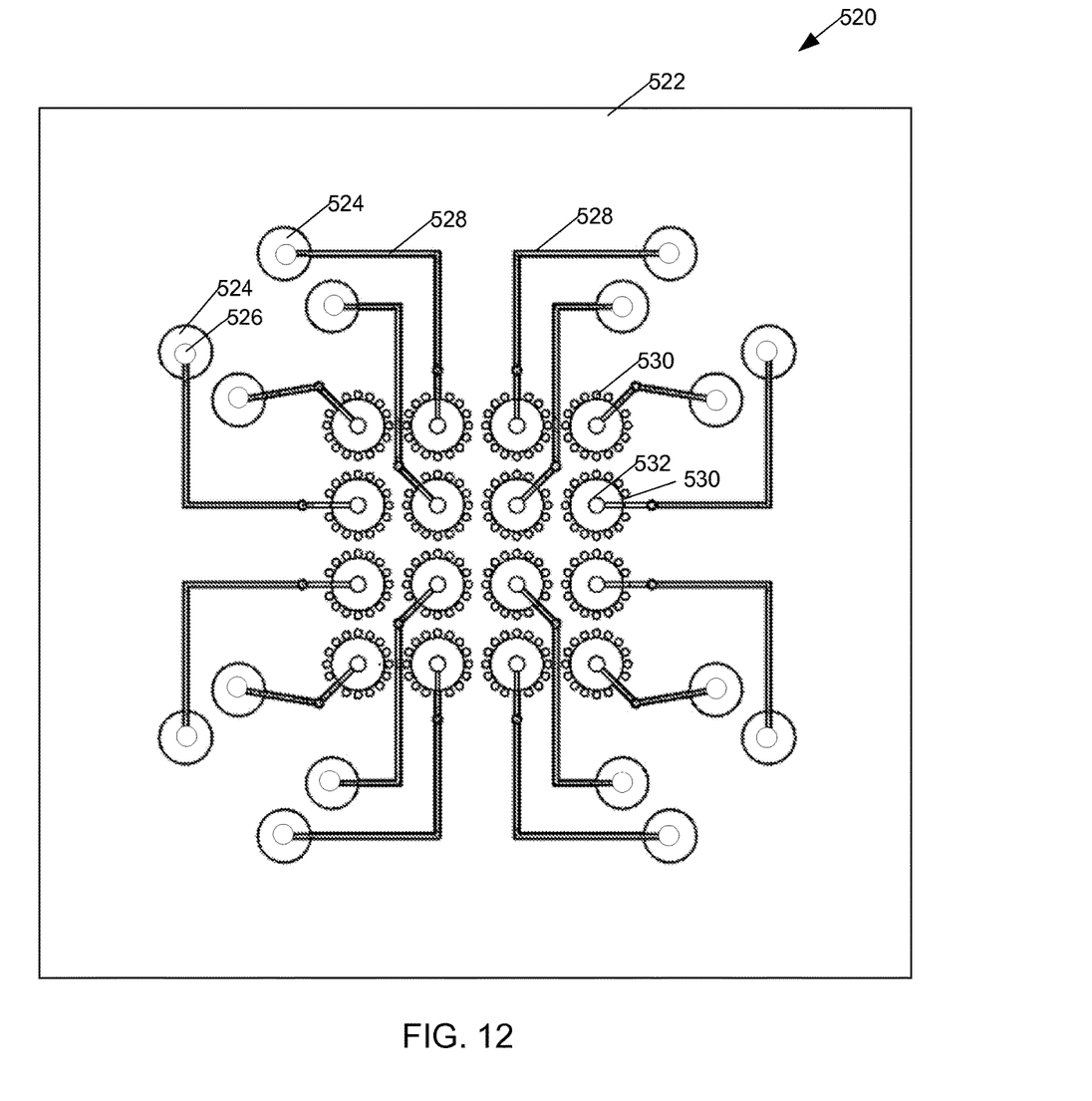
FIG. 12 is a view of the multilayer printed circuit of FIG. 11 showing the coplanar transmission lines of an intermediate layer.

In the embodiment of FIG. 11, an intermediate layer 520, illustrated in FIG. 12, has a ground plane 522 that covers most of its available surface; the ground plane is removed in regions 524 around vias 526 necessary for coupling coplanar transmission lines 528 of the intermediate layer 520 to the top layer where they may connect to multiplexors 504, 506. The ground plane is also removed where necessary to avoid shorting to vias that are necessary for other, non-grounded, signals and for a gap distance, similar to gaps 220, 222, along both sides of the coplanar transmission lines 528. Part-circular rings of vias 530, coupling to ground plane 522, surround each tissue-contact via 532, the tissue-contact vias 532 forming a rectangular array 540.

Figure 13:
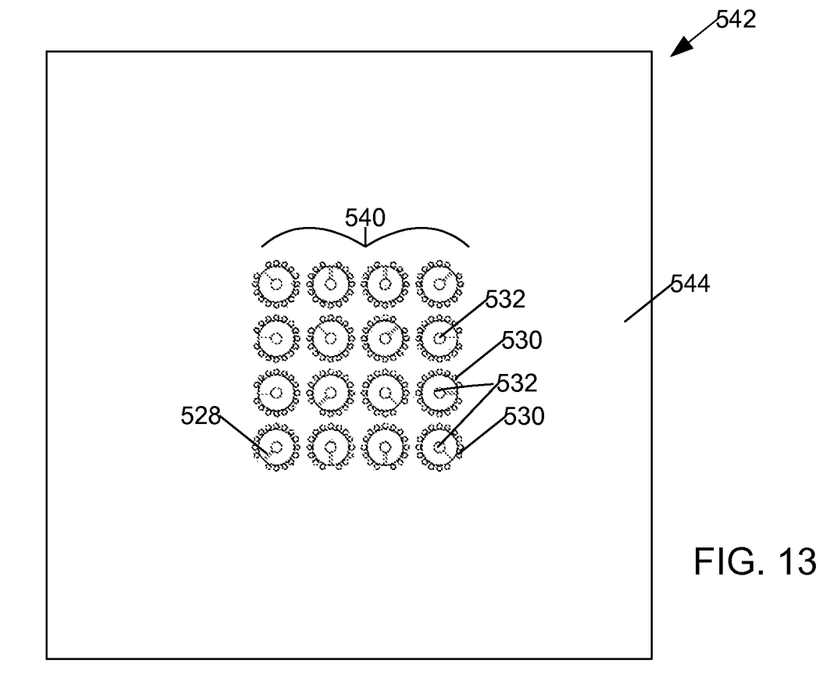
FIG. 13 is a view of a bottom of the multilayer printed circuit of FIG. 11 showing the tissue-contact vias and surrounding part-circle rings of ground vias.

In the embodiment of FIG. 11, the bottom surface 542 of the multilayer board (FIG. 13) also has a ground plane 544. FIG. 13 shows the tissue-contact vias 532 and surrounding part-circle rings of ground vias 530. Since some additional ground plane cutouts to avoid shorts to vias, and vias, associated with other portions of circuitry, including vias 526, may exist in this layer, an insulating coating is then applied to this layer to insulate this layer, with openings in the insulating coating (not shown) to permit part-circle vias 530 and tissue contact vias 532 to touch the tissue.

In use, after calibration, the embodiment of FIG. 11 is placed with the array 540 of tissue-contact vias on a surface of tissue to be analyzed, whether in-vivo in a surgical cavity or on a removed surgical specimen; the computer 107 then scans the tissue by configuring the analog multiplexors 504, 506 to couple a first contact via of contact vias 532 to the network analyzer 102, electrical tissue parameters are measured by the network analyzer and conveyed to the computer 107. The computer 107 executes machine-readable code to repeat configuring the analog multiplexors and reassuring electrical tissue parameters for each contact via 532. The computer then executes machine-readable code to compare measured electrical tissue parameters to a tissue database and to classify tissue according to a tissue type. The computer 107 then displays a map of determined tissue types, highlighting or alarming particular probe locations on the map when tissue is suspected of being cancerous.

Combinations

Some of the combinations of features anticipated are listed below This list of anticipated combinations is not a complete list of possible combinations because many different combinations of features herein described may be used in different embodiments.

In an embodiment designated A, a probe sensor has a printed circuit comprising on a first layer a first coplanar transmission line, and a first ground plane; and on a second layer a second ground plane, and a plated-through contact via and a part-circular ring of plated-through ground vias, the ground vias passing through a substrate between the first ground plane and the second ground plane, the part-circular ring of ground vias surrounding the contact via; wherein the coplanar transmission line has a center conductor coupled to the plated-through contact via.

In an embodiment designated AA, the probe designated A has the coplanar transmission line comprising a central conductor separated from a ground plane by a first gap on a first side, and a second gap on a second side; and wherein the printed circuit board has a plurality of plated-through vias organized as a first row extending along the first ground plane near the first gap and a second row extending along the first ground plane near the second gap, the first and second row of vias coupling the first and second ground planes.

In an embodiment designated AB, the probe designated A or AA wherein the center conductor of the coplanar transmission line further comprises a tapered portion.

In an embodiment designated AC, the probe designated A AA or AB wherein there is a conductor-free ring on the second side of the printed circuit board surrounding the contact via.

In an embodiment designated AD a system for measuring dielectric properties of biological materials comprising a network analyzer electrically coupled through a cable to a probe designated A, AA, AB, or AC.

An embodiment designate AH wherein the probe designated A, AA, AB, AC, AD further has an analog multiplexor. In this embodiment, there is a second coplanar transmission line on the first layer and a second plated-through contact via surrounded by a part-circular ring of plated-through ground vias, and the second coplanar transmission line has a center conductor coupled to the second plated-through contact via. The analog multiplexor operable to connect a network analyzer to a determined coplanar transmission line selected from the first and second coplanar transmission lines.

A system designated B for measuring dielectric properties of biological materials comprising a network analyzer electrically coupled through a cable to a probe, the probe further comprising a printed circuit comprising on a first layer a coplanar transmission line, and a first ground plane; and on a second layer a second ground plane, and a plated-through contact via and part-circular ring of plated-through ground vias passing through a substrate between the first layer and the second layer, the part-circular ring of ground vias surrounding the contact via; the coplanar transmission line has a center conductor coupled to the plated-through contact via.

A method designated AE of measuring dielectric properties of tissue comprising: electrically coupling the contact via of the probe of the system designated AD or B to the tissue; providing a stimulus signal from the network analyzer; and analyzing reflections from the probe-to-tissue interface with the network analyzer.

A method of verifying blood quality designated AF comprising collecting blood in a collection and transfusion set comprising a blood collection reservoir bag having the probe of the system of claims B, AD, or AE, attached thereto, reading a unique identifier from a machine-readable label of the collection and transfusion set; attaching the network analyzer of the system to the probe; obtaining an initial set of electrical parameters of the blood and storing the initial set of electrical parameters with the unique identifier in a memory; detaching the network analyzer from the probe; reading the unique identifier from a machine-readable label of the collection and transfusion set, and using the unique identifier to locate the initial set of electrical parameters; attaching the network analyzer to the probe; obtaining a second set of electrical parameters of the blood and comparing the second set of electrical parameters with the initial set of parameters; and determining whether the second set of electrical parameters differs from the initial set of parameters by more than predetermined limits.

A method designated C of measuring dielectric properties of tissue comprising: Electrically coupling analyzer electronics through a cable to a probe, the probe having a printed circuit with a coplanar transmission line having a central conductor terminating in a plated-through contact via, the contact via partially surrounded by a part-circular ring of ground vias and coupled to a ground conductor of the coplanar transmission line, the contact via being electrically coupled to the tissue; providing a stimulus signal from the analyzer electronics; and observing reflections from the probe-to-tissue interface.

A blood collection and transfusion set designated D comprising: a blood collection reservoir bag having a probe attached thereto, the probe comprising: a printed circuit comprising a coplanar transmission line, a ground plane, a plated-through contact via, and a part-circular ring of ground vias surrounding the contact via; wherein the coplanar transmission line and ground plane are formed on a first layer of the printed circuit, and the contact via and part-circular ring of ground vias are plated with a noncorrosive, conductive, biocompatible material on a second layer of the printed circuit; wherein the probe is adapted for coupling through a cable to a network analyzer for measuring dielectric properties of any blood within the collection reservoir bag.

A method designated E of verifying blood quality comprising: collecting blood in a collection and transfusion set comprising a blood collection reservoir bag having a probe attached thereto, the probe further comprising: a printed circuit comprising a coplanar transmission line, a ground plane, a plated-through contact via, and a part-circular ring of ground vias surrounding the contact via; wherein the coplanar transmission line and ground plane are formed on a first layer of the printed circuit, and the contact via and part-circular ring of ground vias are plated with a noncorrosive, conductive, biocompatible material on a second layer of the printed circuit, wherein the contact via and part-circular ring are disposed to contact blood in the reservoir bag; reading a unique identifier from a machine-readable label of the collection and transfusion set; attaching a network analyzer to the probe; obtaining an initial set of electrical parameters of the blood and storing the initial set of electrical parameters with the unique identifier in a memory; detaching the network analyzer from the probe; reading the unique identifier from a machine-readable label of the collection and transfusion set, and using the unique identifier to locate the initial set of electrical parameters; attaching a network analyzer to the probe; obtaining a second set of electrical parameters of the blood and comparing the second set of electrical parameters with the initial set of parameters; and determining whether the second set of electrical parameters differs from the initial set of parameters by more than predetermined limits.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A probe sensor comprising:
   a printed circuit having, on a first layer of a substrate, a first coplanar transmission line with a center conductor and a first ground plane;
   a second ground plane on a second layer of the substrate;
   a plated-through contact via connected to the center conductor and passing through the substrate; and
   a plurality of plated-through ground vias connecting the first and second ground planes and arranged in a part-circular ring around the plated-through contact via.

2. The probe sensor of claim 1, further comprising:
   on the first layer, at least a second coplanar transmission line having a second center conductor;
   a second plated-through contact via connected to the second center conductor and passing from the first layer to the second layer;
   a plurality of plated-through second ground vias connecting the first and second ground planes and arranged in a part-circular ring around the second plated-through contact via; and
   at least one analog multiplexor coupled configured to connect a network analyzer to a coplanar transmission line selected from the first and second coplanar transmission lines.

3. The probe sensor of claim 1, the center conductor being separated from the first ground plane by a first gap on a first side of the center conductor and a second gap on a second side of the center conductor, the printed circuit further including a plurality of plated-through vias organized as a first row extending along the first ground plane near the first gap and a second row extending along the first ground plane near the second gap, each of the first and second rows of vias connecting the first and second ground planes.

4. The probe sensor of claim 3, further comprising:
   on the first layer, at least a second coplanar transmission line having a second center conductor;
   a second plated-through contact via connected to the second center conductor and passing from the first layer to the second layer;

a plurality of plated-through second ground vias connecting the first and second ground planes and arranged in a part-circular ring around the second plated-through contact via; and at least one analog multiplexor configured to connect a network analyzer to a coplanar transmission line selected from the first and second coplanar transmission lines.

5. The probe sensor of claim 3, the center conductor having (a) a constant first width over a non-zero length of the center conductor within a first portion of the first coplanar transmission line farther from the plated-through contact via, (b) a constant second width over a non-zero length of the center conductor within a second portion of the first coplanar transmission line closer to the plated-through contact via, and (c) decreasing width, along a tapered section of the first coplanar transmission line between the first and second portions, the decreasing width decreasing from the first width at the first portion to the second width at the second portion.

6. The probe sensor of claim 5 further comprising:
on the first layer, at least a second coplanar transmission line having a second center conductor;
a second plated-through contact via connected to the second center conductor and passing from the first layer to the second layer;
a plurality of plated-through second ground vias connecting the first and second ground planes and arranged in a part-circular ring around the second plated-through contact via; and
at least one analog multiplexor coupled to connect a network analyzer to a coplanar transmission line selected from the first and second coplanar transmission lines.

7. The probe sensor of claim 5, the second layer forming a conductor-free ring surrounding the plated-through contact via.

8. The probe sensor of claim 7, further comprising:
on the first layer, at least a second coplanar transmission line having a second center conductor;
a second plated-through contact via connected to the second center conductor and passing from the first layer to the second layer;
a plurality of plated-through second ground vias connecting the first and second ground planes and arranged in a part-circular ring around the second plated-through contact via and; and
at least one analog multiplexor coupled to connect a network analyzer to a coplanar transmission line selected from the first and second coplanar transmission lines.

9. A system for measuring dielectric properties of biological materials comprising a network analyzer electrically coupled through a cable to the probe sensor of claim 7.

10. The probe sensor of claim 1, the first and second layers being disposed on two opposite facing surfaces of the substrate, the substrate being continuous between the first and second layers.

11. A method of measuring dielectric properties of tissue, comprising:
electrically coupling a plated-through contact via of a probe to the tissue, the probe including a printed circuit comprising:
(a) on a first layer of a substrate, a first coplanar transmission line having a center conductor and a first ground plane,
(b) on a second layer of the substrate, a second ground plane,
(c) the plated-through contact via connected to the center conductor and passing between the first layer and the second layer, and
(d) a plurality of plated-through ground vias connecting the first and second ground planes and arranged in a part-circular ring around the plated-through contact via;
providing a stimulus signal from a network analyzer coupled to the probe via a cable; and
analyzing reflections from interface between the probe and the tissue with the network analyzer.

12. The method of claim 11, wherein:
(a) the center conductor is separated from the first ground plane by a first gap on a first side of the center conductor and a second gap on a second side of the center conductor;
(b) the printed circuit further includes a plurality of plated-through vias organized as a first row extending along the first ground plane near the first gap and a second row extending along the first ground plane near the second gap, each of the first and second rows of vias coupling the first and second ground planes;
(c) the center conductor has (i) a constant first width over a non-zero length of the center conductor within a first portion of the first coplanar transmission line farther from the plated-through contact via, (ii) a constant second width over a non-zero length of the center conductor within a second portion of the first coplanar transmission line closer to the plated-through contact via, and (iii) decreasing width, along a tapered section of the first coplanar transmission line between the first and second portions, the decreasing width decreasing from the first width at the first portion to the second width at the second portion; and
(d) the second layer forms a conductor-free ring surrounding the plated-through contact via.

13. The method of claim 11, wherein the probe further includes (e) on the first layer, at least a second coplanar transmission line having a second center conductor, (f) a second plated-through contact via connected to the second center conductor and passing from the first layer to the second layer, and (g) a plurality of plated-through second ground vias connecting the first and second ground planes and arranged in a part-circular ring around the second plated-through contact via, the method further comprising:
connecting, using an analog multiplexor, the network analyzer to a coplanar transmission line selected from the first and second coplanar transmission lines.

14. A system for measuring dielectric properties of biological materials, comprising:
a network analyzer;
a probe electrically coupled through a cable to the network analyzer, the probe including a printed circuit comprising:
(a) on a first layer of a substrate, a first coplanar transmission line with a center conductor and a first ground plane,
(b) on a second layer of the substrate, a second ground plane,
(c) a plated-through contact via connected to the center conductor and passing between the first layer and the second layer, and (d) a plurality of plated-through ground vias connecting the first and second ground planes and arranged in a part-circular ring around the plated-through contact via.

15. The system of claim 14, further comprising:
on the first layer, at least a second coplanar transmission line having a second center conductor;
a second plated-through contact via connected to the second center conductor and passing from the first layer to the second layer;
a plurality of plated-through second ground vias connecting the first and second ground planes and arranged in a part-circular ring around the second plated-through contact via; and
at least one analog multiplexor operable to connect the network analyzer to a coplanar transmission line selected from the first and second coplanar transmission lines.

16. A method of measuring dielectric properties of tissue, comprising:
electrically coupling analyzer electronics through a cable to a probe, the probe including a printed circuit with a coplanar transmission line having a center conductor terminating in a plated-through contact via electrically connected to the tissue, the contact via partially surrounded by a plurality of ground vias arranged in a part-circular ring and coupled to a ground conductor of the coplanar transmission line;
providing a stimulus signal from the analyzer electronics; and
observing reflections from interface between the probe and the tissue.

17. A blood collection and transfusion set, comprising:
a blood collection reservoir bag;
a probe attached to the blood collection reservoir bag and configured for coupling through a cable to a network analyzer for measuring dielectric properties of blood within the collection reservoir bag, the probe comprising:
a printed circuit including (a) on a first layer, a coplanar transmission line having a ground plane, (b) a plated-through contact via, and (c) a plurality of ground vias arranged in a part-circular ring around the plated-through contact via; the contact via and the ground vias being plated with a noncorrosive, conductive, biocompatible material on a second layer of the printed circuit.

18. A method of verifying blood quality, comprising:
collecting blood in a collection and transfusion set comprising a blood collection reservoir bag having a probe attached thereto, the probe comprising a printed circuit including (a) on a first layer, a coplanar transmission line having a center conductor and a ground plane, (b) a plated-through contact via, and (c) a plurality of ground vias arranged in a part-circular ring around the plated-through contact via;
reading a unique identifier from a machine-readable label of the collection and transfusion set;
attaching a network analyzer to the probe;
obtaining an initial set of electrical parameters of the blood and storing the initial set of electrical parameters with the unique identifier in a memory;
detaching the network analyzer from the probe;
reading the unique identifier from a machine-readable label of the collection and transfusion set, and using the unique identifier to locate the initial set of electrical parameters;
attaching a network analyzer to the probe;
obtaining a second set of electrical parameters of the blood and comparing the second set of electrical parameters with the initial set of parameters; and
determining whether the second set of electrical parameters differs from the initial set of parameters by more than predetermined limits.

19. The method of claim 18, wherein the printed circuit further includes (d) on the first layer, at least a second coplanar transmission line having a second center conductor, (e) a second plated-through contact via connected to the second center conductor and passing from the first layer to the second layer, and (f) a plurality of plated-through second ground vias connecting the first and second ground planes and arranged in a part-circular ring around the second plated-through contact via, the method further comprising:
connecting, using an analog multiplexor, the network analyzer to a coplanar transmission line selected from the first and second coplanar transmission lines.

20. The method of claim 18, wherein the plated-through contact via and part-circular ring of the ground vias are plated with a noncorrosive, conductive, biocompatible material on a second layer of the printed circuit, and wherein the plated-through contact via, and the ground vias are disposed to contact blood in the reservoir bag.

21. The method of claim 18, wherein:
(a) the center conductor is separated from the first ground plane by a first gap on a first side of the center conductor and a second gap on a second side of the center conductor;
(b) the printed circuit further includes a plurality of plated-through vias organized as a first row extending along the first ground plane near the first gap and a second row extending along the first ground plane near the second gap, each of the first and second rows of vias coupling a first ground plane to a second ground plane on a second layer of the printed circuit;
(c) the center conductor has (i) a constant first width over a non-zero length of the center conductor within a first portion of the first coplanar transmission line farther from the plated-through contact via, (ii) a constant second width over a non-zero length of the center conductor within a second portion of the first coplanar transmission line closer to the plated-through contact via, and (iii) decreasing width, along a tapered section of the first coplanar transmission line between the first and second portions, the decreasing width decreasing from the first width at the first portion to the second width at the second portion; and
(d) the second layer forms a conductor-free ring surrounding the plated-through contact via.

\* \* \* \* \*

UNITED STATES PATENT AND TRADEMARK OFFICE
CERTIFICATE OF CORRECTION

PATENT NO.        : 9,880,118 B2
APPLICATION NO.   : 14/117368
DATED             : January 30, 2018
INVENTOR(S)       : Paul M. Meaney et al.

Page 1 of 1

It is certified that error appears in the above-identified patent and that said Letters Patent is hereby corrected as shown below:

In the Specification

At Column 1, Lines 13-16:
"This invention was made with government support under Grant #POI-CA080139 awarded by the National Institutes of Health/National Cancer Institute. The government has certain rights in the invention."

Should read:
-- This invention was made with government support under grant number P01 CA080139 awarded by the National Institutes of Health. The government has certain rights in the invention. --

Signed and Sealed this
Third Day of December, 2019

Andrei Iancu
*Director of the United States Patent and Trademark Office*